United States Patent [19]

Schulz et al.

[11] Patent Number: 5,702,709
[45] Date of Patent: Dec. 30, 1997

[54] SKIN ALLERGEN AND IRRITANT BARRIER LOTION

[75] Inventors: Anthony A. Schulz, Floyds Knobs, Ind.; David J. Buddrus, Dallas, Tex.

[73] Assignee: Enviroderm Pharmaceuticals, Inc., Louisville, Ky.

[21] Appl. No.: 423,099

[22] Filed: Apr. 18, 1995

[51] Int. Cl.$^6$ .................................................. A61K 9/48
[52] U.S. Cl. .................................... 424/401; 514/862
[58] Field of Search ........................... 424/401; 514/862

[56] References Cited

U.S. PATENT DOCUMENTS

| | | | |
|---|---|---|---|
| 4,659,571 | 4/1987 | Laba | 424/65 |
| 4,861,584 | 8/1989 | Powell et al. | 424/79 |
| 5,017,361 | 5/1991 | Powell et al. | 424/46 |
| 5,120,716 | 6/1992 | Miyazawa et al. | 514/23 |

OTHER PUBLICATIONS

Journal of the American College of Toxicology 1(2), 71–83 (1982), "Final Report on the Safety Assessment of Quaternium–18 Hectorite and \Quaternium–18 Bentonite".

Balsam, M.S., et al., "Cosmetics, Science & Technology", 2nd ed., vol. 1, pp. 195–196, 1972.

Gosselin, R.E., et al., "Clinical Toxicology of Commercial Products", Fifth Edition, Williams & Wilkins, Baltimore, 1984, p. V–633.

*Primary Examiner*—Jyothsan Venkat
*Attorney, Agent, or Firm*—Vorys, Sater, Seymour and Pease

[57] ABSTRACT

A lotion capable of protecting the skin from the effects of exposure to irritants and allergens, particularly those produced by toxic plants such as poison ivy, has the following composition, wherein the proportions are by weight:

| | |
|---|---|
| organophilic clay | 3.0–10.0% |
| volatile alcoholic solvent | 20.0–30.0% |
| cosmetically acceptable inert emollient vehicle | 15.0–25.0% |
| thickener | 2.0–10.0% |
| water | q.s.p. 100.0% |

14 Claims, 1 Drawing Sheet

Plot of Mean Poison Ivy Reaction Scores

Day After Allergen Challenge

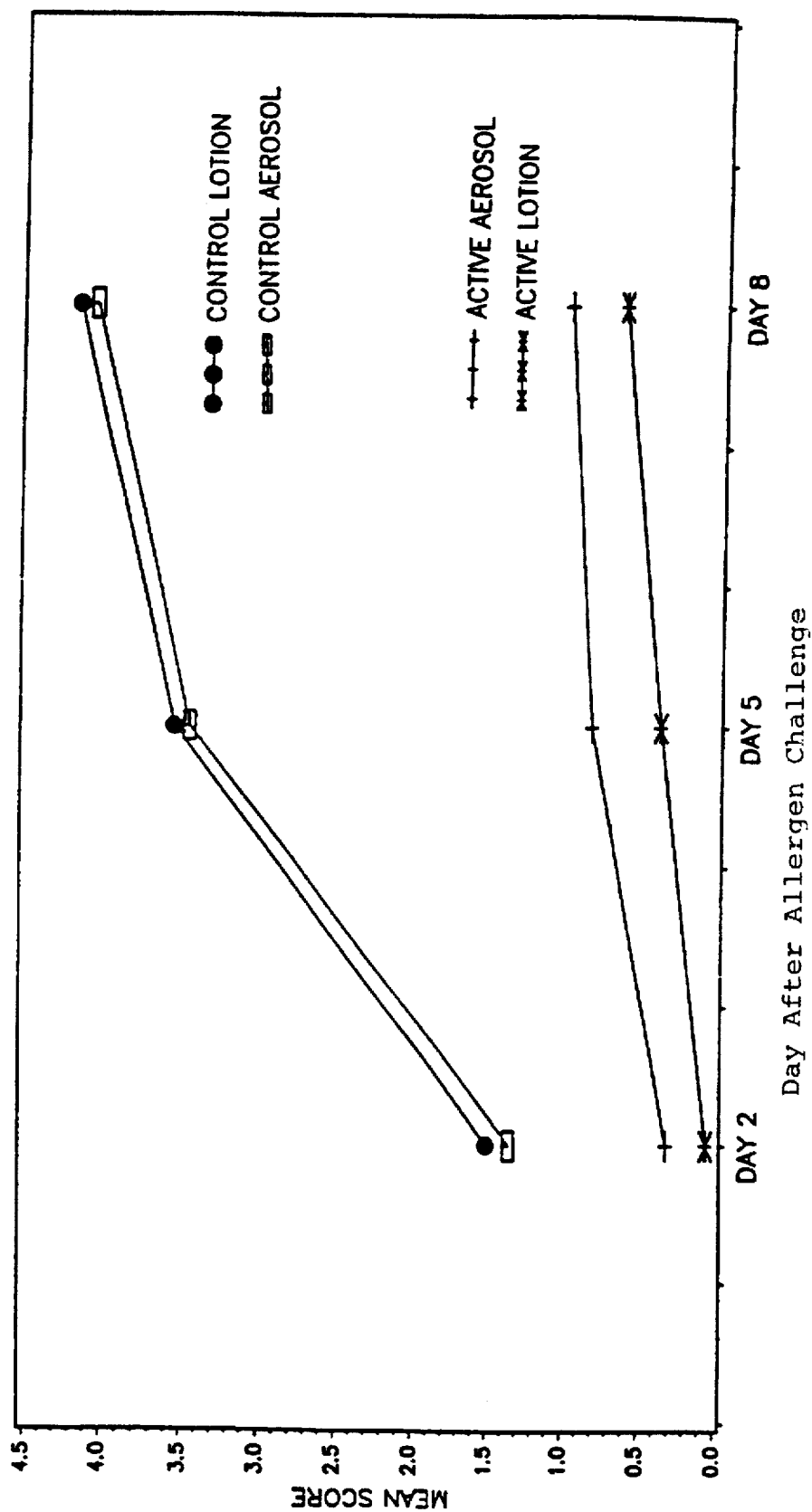

SKIN ALLERGEN AND IRRITANT BARRIER LOTION

BACKGROUND OF THE INVENTION

1. Field of the Invention

This invention relates to methods of protecting the skin from contact with allergens and irritants and compositions for use in such methods and more particularly to compositions that protect the skin from contact dermatitis by allergens and irritants and, in particular, from allergic contact dermatitis caused by contact with poison ivy and similar toxic plants.

2. Brief Description of the Prior Art

Contact dermatitis is caused by irritants and allergens to which a sensitive individual is exposed. While treatment with emollients and antiinflammatories is often effective against such dermatitis, it is useful or preferable to prevent the dermatitis by the skin from contact with the irritant or allergen, especially when encounters with such materials can be anticipated. Although in many cases protective clothing can be worn, such are not always practical.

A particular type of allergic contact which is widely prevalent and can, to some extent, be anticipated is that caused by exposure of sensitized individuals plants of the Rhus family such as poison ivy, poison oak, and poison sumac. The dermatitis produced by such allergic is a hazard of outdoor recreational activities and is troublesome for persons whose work brings them into areas such plants grow. The problem is particularly acute for forest fighters, forest workers, agricultural workers and the like, whose work prevents them from taking steps to avoid with the toxic plants.

It is known that the agent that causes allergic contact dermatitis associated with poison ivy and toxic plants is an oily material known as urushiol which is in the leaves, stems, etc., of the plants. Urushiol is a of phenolic compounds having a long unsaturated alkyl chain of from 9–15 carbon atoms. Urushiol acts as an antigen chain it comes in contact with the skin of a person susceptible to being sensitized. It is estimated that approximately seventy percent of the North American populace is susceptible to being sensitized to urushiol with repeated exposure. After a sensitizing exposure, subsequent exposure to urushiol the characteristic itching and vesiculation of a poison ivy rash.

Because desensitization treatments are difficult and not proven to be effective, prevention of poison dermatitis has focused on preventing contact of the antigen with the skin. Sensitized individuals are encouraged to contact with the poisonous plants. However, as pointed out above, some individuals cannot avoid such contact because of the nature of their work. Various alleged poisonivy/oak preventative creams, ointments and lotions have been marketed but none has been proven to be effective and fully cosmetically acceptable. The barrier materials used hitherto are typically greasy and interfere with perspiration. Accordingly, the use of these barrier materials is somewhat unpleasant at best and presents special problems for fire fighters who must work under conditions of great heat while wearing protective clothing.

An aerosol spray formulation incorporating certain activated organophilic clay materials has been disclosed in U.S. Pat. No. 4,861,584, to Powell et al., the entire disclosure of which is incorporated herein by reference. This formulation has shown effectiveness in preventing or diminishing the allergic contact dermatitis due to urushiol-bearing plants. However, the aerosol formulation is somewhat difficult to apply evenly and the organophilic clay component therein tends to dry the skin.

Accordingly, a need has continued to exist for a formulation that is easy to apply to the skin and will prevent contact dermatitis, especially that caused by contact with poison ivy and similar toxic plants and will not dry the skin.

SUMMARY OF THE INVENTION

This problem has now been solved by a lotion formulation having the following composition, wherein the proportions are by weight:

| | |
|---|---|
| organophilic clay | 3.0–10.0% |
| volatile alcoholic solvent | 20.0–30.0% |
| cosmetically acceptable inert emollient vehicle | 15.0–25.0% |
| thickener | 2.0–10.0% |
| water | q.s.p. 100.0% |

The invention also encompasses a method of protecting the skin against dermatitis caused by contact with allergens and irritants by applying to the skin an amount of the lotion of the invention effective to prevent such dermatitis.

Accordingly, it is an object of the invention to provide a protective lotion for preventing allergic and irritant contact dermatitis.

A further object is to provide a lotion that will protect the skin from allergic contact dermatitis due to contact with poison ivy, poison, oak, poison sumac and the like.

A further object is to provide a lotion that will protect the skin from contact dermatitis due to contact with irritants.

A further object is to provide a method for protecting the skin from dermatitis caused by contact with allergens and irritants.

Other objects of the invention will become apparent from the description of the invention which follows.

BRIEF DESCRIPTION OF THE DRAWING

The sole FIGURE illustrates the results of a comparison of the protective effect of the lotion of this invention against topically applied urushiol, the allergen of toxic plants such as poison ivy, with the protective effect of an aerosol concentrate of the prior art.

DETAILED DESCRIPTION OF THE INVENTION AND PREFERRED EMBODIMENTS

The protective lotion of the invention comprises an organophilic clay that acts as an adsorbent and barrier for urushiol allergen, as well as a barrier that protects the skin from contact with irritants and allergens, dispersed in a cosmetically acceptable emollient vehicle that permits the material to be spread conveniently and evenly over the skin to be protected. The emollient vehicle should preferably be inert with respect to the organophilic clay, i.e., it should be devoid of materials that will deactivate the adsorptive or barrier properties of the organophilic clay for allergens of the urushiol type. The lotion should have a viscosity that permits easy spreading of the material without excessive running or dripping. To this end the lotion incorporates a swellable hydrophilic clay thickener in an aqueous-alcoholic solvent for the emollient vehicle. The concentration of the thickener is adjusted to provide the proper viscosity.

The organophilic clay that comprises the barrier and/or allergen adsorbent material in the protective lotion of this invention may be any conventional organophilic clay of commerce suitable for drug use. Such organophilic clays are well known and can be prepared from any of the clays of the smectite class that are known to swell in water and hydrophilic solvents to form viscous suspensions. Suitable clays include naturally occurring montmorillonite, bentonite, beidellite, hectorite, saponite and stevensite, and their synthetically made counterparts. These clays have a lamellar structure wherein alkali metal ions are distributed between the lamellae. Treatment of the clay with long-chain organic amphiphilic compounds such as long-chain quaternary amines results in exchange of the alkali metal ions by cationic organic molecules and thereby renders the clay organophilic.

The quaternary ammonium compounds used in preparing the organophilic clay component of the protective lotion typically have one or two long-chain substituents, e.g., 14–20 carbon atoms, and two or three short-chain substituents such as methyl groups. A preferred quaternary ammonium compound is dimethyl dihydrogenated tallow ammonium chloride. Because the tallow contains a large proportion of stearic acid, which contains 18 carbon atoms, the resulting clay is often referred to as a quaternium 18 clay, e.g., quaternium 18 bentonite, or quaternium 18 hectorite. The composition and preparation of such organophilic clays is discussed in U.S. Pat. No. 4,861,584. A preferred organophilic clay for use in the lotion of this invention is quaternium 18 bentonite.

The organophilic clay used in the lotion of this invention is preferably activated by thorough dispersion with a solvent such as propylene carbonate which is known to increase the adsorptive capability of the clay for organic materials.

The organophilic clay is present in the protective lotion in the proportion of 3.0–10.0% by weight, preferably 4.0–6.0% by weight and more preferably about 5.0% by weight.

The lotion of the invention comprises a cosmetically acceptable emollient, liquid at room temperature and soluble in the alcoholic solvent, that does not react with the organophilic clay to deactivate its barrier properties and adsorptive capacity for urushiol and similar antigens. Typically, such emollient vehicles will include esters having relatively short alkyl groups such as loweralkyl esters of dibasic acids, e.g., diisopropyl adipate, diisopropyl sebacate, and the like; loweralkanoic acid esters of di- and trihydroxy alcohols, e.g., propylene glycol dicaprylate/dicaprate, or caprylic/capric triglyceride, and the like. Emollients having long terminal hydrocarbyl chains would be expected to adsorb to the organophilic clay and thereby reduce its activity as an adsorbent for the urushiol allergen. Accordingly such long-chain emollients are less preferred. A preferred emollient is diisopropyl adipate.

The volatile alcohol solvent used in the allergen protective lotion of the invention can be any cosmetically acceptable volatile alcohol. Typically, the volatile alcohol will be ethanol or isopropyl alcohol. The volatile alcoholic solvent is present in the lotion of the invention in an amount of from about 20.0% to about 30.0%, by weight, preferably from about 23.0% to about 27.0% by weight, and most preferably about 25.0% by weight.

The thickener used in the protective lotion of the invention can be an organic polymeric thickener such as is conventionally used in aqueous pharmaceutical solutions. Such thickeners include hydroxyethyl cellulose, hydroxypropyl cellulose, hydroxypropyl methylcellulose, methylcellulose, carboxymethylcellulose sodium, poly(vinyl alcohol), poly(vinylpyrrolidone), poly(acrylic acid) sodium salt, and the like. Natural gums such as xanthan gum, carrageenan, gum tragacanth and the like are also useful as thickeners. The thickener may also be a colloidal dispersion of a hydrophilic clay such as naturally occurring montmorillonite, bentonite, heidellite, hectorite, saponite, stevensite, or the like, and their synthetically produced analogs. A preferred thickener is bentonite. The thickener is present in the lotion of the invention in an amount sufficient to provide a viscosity suitable for convenient application and spreading on the skin. It will be recognized by those skilled in the art that, because the thickening agents used in dermatological lotions often exhibit non-Newtonian rheology, the lotions are often thixotropic and cannot be characterized by a single numerical viscosity. The skilled practitioner will also recognize that, because different thickeners have different effects on the viscosity of aqueous media, the amount of each thickener used will be adjusted to give an appropriate viscosity to the lotion. When a colloidal hydrophilic clay, e.g., bentonite, is used as a thickener, its concentration will typically range from about 2.0% to about 10.0% by weight, preferably from about 3.0% to about 7.0% by weight and most preferably about 5.0% by weight.

In order to protect the skin from dermatitis due to contact with allergens such as urushiol or other allergens and irritants, the lotion of the invention is spread over the portion of the skin likely to come into contact with the sensitizing or irritant material in an amount to provide a generally uniform layer of the organophilic clay adsorbent and/or barrier material over the treated area. After application the volatile alcohol component of the lotion evaporates and the emollient vehicle is largely absorbed into the skin, leaving thereon a coating of the organophilic clay which provides a barrier against environmental allergens and irritants. It is believed that the layer of organophilic clay is especially useful protection against urushiol-type allergens because its adsorptive capacity for such materials immobilizes them, thereby keeping them from contacting the skin at the point of initial contact with the plant vector as well as preventing spreading to other locations on the skin.

Typically, an amount of the lotion that provides a coating of about 0.25 milligrams of the organophilic clay adsorbent per square centimeter of skin surface will provide significant protection against dermatitis caused by contact with urushiol-producing plants of the poison ivy family.

EXAMPLE

This example illustrates the superior protection against urushiol-provoked contact dermatitis achieved with the lotion of this invention as compared with an aerosol formulation of the prior art.

An allergen blocking lotion of the invention was prepared having the following formula, wherein all percentages are by weight:

| | |
|---|---|
| quaternium 18 bentonite | 5.0% |
| SD alcohol 40-2 | 25.0% |
| diisopropyl adipate | 20.0% |
| bentonite NF | 5.0% |
| methyl paraben NF | 0.100% |
| benzyl alcohol NF | 0.200% |
| purified water USP | 44.7% |

A concentrate of the preparation used in the aerosol formulation of the prior art as described in Example 1 of U.S. Pat. No. 4,861,584 was prepared having the following composition, wherein the percentages are by weight:

| quaternium 18 bentonite | 11.3% |
|---|---|
| SD alcohol 40-2 | 4.3% |
| cyclomethicone | 84% |

In the preparation of the aerosol formulation of the prior art, as explained in Example 1 of U.S. Pat. No. 4,861,584, the concentrate is loaded into an aerosol container and pressurized with a hydrocarbon propellant to produce a ratio of concentrate to propellant of about 30:70 by weight. The aerosol formulation is designed to be applied to the skin by a conventional spraying procedure that leaves a coating of the concentrate on the skin after any propellant has evaporated. Such a formulation has been shown to be clinically effective. However, when such a concentrate is applied by spraying, it is difficult to reproduce the amount applied to the skin with sufficient precision for scientific comparison studies. Accordingly, in this comparison study the aerosol concentrate was applied to the skin directly in a measured amount.

Volunteers known to be sensitive to plants of the poison ivy family were selected and, after informed consent, the following experimental protocol was followed.

The experiment was designed so that each subject served as his/her own control. On Day 0 of the study, two treatment areas, 5 cm by 10 cm, were designated on the volar surface of each forearm. On one forearm the sites were randomly designated for a control and for application of the lotion of the invention; on the other arm the sites were randomly designated for a control and for application of the aerosol concentrate of the prior art. The experiment was then carried out by applying the lotion of the invention, aerosol concentrate and the urushiol allergen to the designated experimental skin areas and evaluating the results following the protocol described below.

The 5% quaternium 18 bentonite ("Q18B") lotion of the invention was applied by placing 0.35 ml of the lotion, measured by syringe, in the center of the 50 square cm test area and spreading as evenly as possible with the fingertips over the test site. This procedure is intended to produce a film of Q18B at a coating weight of about 0.25 milligrams per square centimeter of skin area.

The 11.3% Q18B aerosol concentrate of the prior art was applied by placing 18.20 microliters, measured by micropipette, in the center of the 50 square cm test area and spreading as evenly as possible with a glass rod over the test site. This procedure is also designed to produce a film of Q18B having a coating weight of about 0.25 milligrams per square centimeter of skin area.

The treated sites were allowed to dry for a period of one hour before challenge with the urushiol allergen solution. The allergen challenge solution was prepared by diluting a standard commercial preparation of urushiol (Hollister-Steir Poison Ivy/Oak Oleo, Lot # D 15683 M) with 95% ethanol such that the concentration of the resulting solution was 50% of that of the original Hollister-Steir material. Allergy test patches were centered on three-inch strips of porous tape. One hour before application to the skin, 10.0 microliter portions of the test allergen solution were applied to each of the test patches and the patches were allowed to dry. At Time 0 one patch was applied to each of the designated test sites and allowed to remain in contact with the skin for a period of four hours. At Time 4 (four hours after application) the patches were removed and the test sites were washed with mild soap and water. The test subjects were then allowed to return to normal activity with instructions to return in two days for evaluation of the test sites.

On Day 2, approximately 48 hours after the test patches were applied to the skin, the condition of the test sites was scored according to the following scale:

| 0 | no reaction |
|---|---|
| +/− | questionable reaction |
| 1+ | erythema only |
| 2+ | erythema with edema |
| 3+ | erythema, edema and beginning vesiculation, involving less than 25% of the test site |
| 4+ | as in 3+, but vesicles involving 25 to 50% of the treatment site |
| 5+ | as in 3+, but vesicles involving 50 to 75% of the treatment site |
| 6+ | as in 3+, but vesicles confluent in a circular pattern over the test site |
| 7+ | erythema, edema, vesiculation plus evidence of ulcerative breakdown |

On Study Day 5, approximately 120 hours after application of the test patches, the test sites were again evaluated and scored as on Study Day 2. Finally, on Study Day 8, approximately 192 hours after the application of the test patches, the test sites were again evaluated and scored.

Evaluation of the results by statistical tests established that non-parametric statistical methods should be used in analyzing the results. Accordingly the sign test was used in which each pair of test sites, treated and control, was compared and assigned a sign, "plus" if the score of the treated site was greater than that of the control site, and "minus" if the score of the treated site was less than that of the control site. The sign test then compares the number of "minus" pairs versus the number of "plus" pairs, discounting the "ties", to see if the number of cases in which the treated site had a lower score than its control was significantly different from the number of cases in which the control site had the lower score. For both the lotion formula and the aerosol concentrate, there was a statistically significant difference between the treated sites and the control sites ($p<0.0001$ in each case) on Days 2, 5 and 8.

In order to compare the protective effect of the lotion formula of this invention with that of the aerosol concentrate, the mean scores for each formulation were calculated and plotted against time. The results can be seen in FIG. 1. Lower scores indicate greater protection. It can be seen that the control sites for both the lotion and the aerosol concentrate have essentially the same scores for each evaluation day. The corresponding scores for the test sites treated with the aerosol concentrate and the lotion formula are both substantially lower than the controls, indicating that each formulation produces significant protection from dermatitis caused by exposure to urushiol. However, it is clear that the scores for the lotion formula are uniformly lower than those for the aerosol concentrate formula for all of the test days.

The results of this experiment indicate that the lotion formula of this invention produces protection of the skin from dermatitis due to contact with urushiol that is superior to the protection provided by the aerosol concentrate formula of the prior art.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

I claim:

1. A lotion for protecting the skin from contact with allergens and irritants consisting essentially of

| | |
|---|---|
| quaternium-18 bentonite | 3.0–10.0% |
| volatile alcoholic solvent | 20.0–30.0% |
| loweralkyl ester of a lower dibasic acid | 15.0–25.0% |
| colloidal clay thicknener selected from the group consisting of naturally occurring montmorillonite, bentonite, beidellite, hectorite, saponite and stevensite | 2.0–10.0% |
| water | q.s.p. 100.0% | wherein all percentages are by weight.

2. The lotion of claim 1 wherein said quaternium-18 bentonite is present in an amount of about 3.0% to about 7.0% by weight.

3. The lotion of claim 2 wherein said quaternium-18 bentonite is present in an amount of about 5.0% by weight.

4. The lotion of claim 1 wherein said volatile alcoholic solvent is present in amount of about 23.0% to about 27.0% by weight.

5. The lotion of claim 4 wherein said volatile alcoholic solvent is present in amount of about 25.0% by weight.

6. The lotion of claim 1 wherein said loweralkyl ester of a lower dibasic acid is present in an amount of about 18.0% to about 22.0% by weight.

7. The lotion of claim 6 wherein said loweralkyl ester of a lower dibasic acid is present in an amount of about 20.0% by weight.

8. The lotion of claim 1 wherein said colloidal clay thickener is present in an amount of about 3.0% to about 7.0% by weight.

9. The lotion of claim 8 wherein said colloidal clay thickener is present in an amount of about 5.0% by weight.

10. The lotion of claim 1 wherein said quaternium-18 bentonite is activated.

11. The lotion of claim 1 wherein said volatile alcoholic solvent is ethanol.

12. The lotion of claim 1 wherein said emollient vehicle is diisopropyl adipate.

13. The lotion of claim 1 wherein said colloidal clay thickener is bentonite.

14. A lotion for protecting the skin from contact with allergens and irritants comprising

| | |
|---|---|
| quaternium 18 bentonite | 5.0% |
| cosmetically acceptable denatured ethanol | 25.0% |
| diisopropyl adipate | 20.0% |
| bentonite | 5.0% |
| methyl paraben | 0.100% |
| benzyl alcohol | 0.200% |
| purified water | 44.7% |

* * * * *